United States Patent
Mosconi

(10) Patent No.: US 8,211,481 B2
(45) Date of Patent: Jul. 3, 2012

(54) METHOD FOR PREPARING A HYPERICUM EXTRACT IN NEEM OIL AND A SUBSTANCE SO OBTAINED

(75) Inventor: Marco Mosconi, Rimini (IT)

(73) Assignee: Moses S.r.l., Falciano (SM)

( * ) Notice: Subject to any disclaimer, the term of this patent is extended or adjusted under 35 U.S.C. 154(b) by 188 days.

(21) Appl. No.: 12/671,237

(22) PCT Filed: Jul. 31, 2008

(86) PCT No.: PCT/EP2008/060104
§ 371 (c)(1),
(2), (4) Date: Jan. 29, 2010

(87) PCT Pub. No.: WO2009/016247
PCT Pub. Date: Feb. 5, 2009

(65) Prior Publication Data
US 2010/0189823 A1    Jul. 29, 2010

(30) Foreign Application Priority Data
Aug. 1, 2007 (SM) .................. SM-A-200700032

(51) Int. Cl.
*A61K 36/38* (2006.01)
*A61K 36/58* (2006.01)
(52) U.S. Cl. .................. 424/730; 424/761; 424/778
(58) Field of Classification Search .......... None
See application file for complete search history.

(56) References Cited

FOREIGN PATENT DOCUMENTS

| EP | 0415327 A | 3/1991 |
|----|-----------|--------|
| EP | 1197219 A | 4/2002 |
| FR | 2864447 A | 7/2005 |
| RU | 2008914 C1 * | 3/1994 |
| WO | WO2006/013607 A | 2/2006 |

OTHER PUBLICATIONS

English translation of EP 1197219—Apr. 2002.*
International Search Report, Sep. 24, 2009.
Kulevanova, S. et al., "Determination of Total Flavanoids and Quercitin in Hyperici Herba and its Aqueous, Aqueous-Ethanolic and Oil Extracts", Acta Pharmaceutica, Zagreb, HR, vol. 50, No. 1, Jan. 1, 2000, pp. 29-37, XP009033700.
"Final Report on the Safety Assessment of Hypericum Perforatum Extract and Hypericum Perforatum Oil", International Journal of Toxicology, Taylor and Francis, Washington D.C., U.S., vol. 20, No. Suppl. 02, Jan. 1, 2001, pp. 31-39 XP009016121.

* cited by examiner

*Primary Examiner* — Susan Hoffman
(74) *Attorney, Agent, or Firm* — William J. Sapone; Coleman Sudol Sapone P.C.

(57) ABSTRACT

A method for making a *Hypericum perforatum* extract in Neem oil, provides of:
  combining an amount of *Hypericum* flowers and/or capsules with a quantity of Neem oil;
  introducing into a reactor the mixture made of the amounts of *Hypericum* flowers and/or capsules and of Neem oil;
  maintaining the mixture vacuum, under agitation for a predefined time and temperature. A composition includes Neem oil and *Hypericum* flowers and/or capsules. Such composition includes moreover a solvent or a mixture of solvents.

15 Claims, No Drawings

METHOD FOR PREPARING A HYPERICUM EXTRACT IN NEEM OIL AND A SUBSTANCE SO OBTAINED

TECHNICAL FIELD

This invention relates to medical-surgical devices, in particular refers to a method for the preparation of a *Hypericum perforatum* extract (*Hypericum*) in Neem oil and to a substance so obtained.

BACKGROUND ART

It is known that the oleolito or the *hypericum perforatum* extract has anti-inflammatory effect, antiseptic and cicatrizing in the external wounds, ulcers and burns.

It is furthermore known that the Neem oil has cicatrizing, biocide, anti inflammatory, myasis insect repellent and not proprieties.

For example it is known in WO 2006/013607 that the oil mixture of Neem and the oily extract of *Hypericum perforatum* add the bioactive characteristics verified in the single components of the mixture.

Said diluting effect precludes to think equivalent the biologic and biocide properties, of single obtainable compositive mixtures, because the biologic property is molecular, depends on the structure and depending on dose.

In such document WO 2006/013607, for indicated preparation modality, the *hypericum* oleolito cannot certainly satisfy the reproducibility criterion of the obtained oleolito results, considering the loss of the process conditions (temperature, time, lighting degree, agitation, drugs/oil ratio), to satisfy the criterion of a minimum reproducibility of the oleolito molecular composition.

Moreover in the preparation so obtained already at 16° C. develops turbidity because of hydrocarbons, fat acids, etc. precipitation, so modifying the spreading and the use easiness of the preparation. This fact decreases the potentiality in the space-time, in relation to the climate.

Moreover the spagyric maceration used in the extraction process according to document WO2006/013607 is subjected to climatic factor (light, temperature) variability and is subjected to process variable times.

DISCLOSURE OF THE INVENTION

Object of this invention is to propose an industrial extraction method of the bioactive substances of *Hypericum perforatum* flowers and infructescences (capsules) using as extracting solution of the Neem oil without using other oil for the maceration.

Further object is to increase the extraction method for example by using a solvent.

An additional aim is to obtain *Hypericum* extracts directly in Neem oil concentrates and with greater applicability range in function of the temperature.

An additional aim is furthermore to offer a method highly easy and economically advantageous.

BEST MODE OF CARRYING OUT THE INVENTION

The method object of the present invention consists in putting the fresh, frozen, dried, lyophilized *Hypericum* flowers, and the infructescences (capsules), or their mixtures into a reactor, consisting of a steel container, equipped with central rotatory axis carrying, inserted on the axis, agitation blades, that can to be rotate with variable speed. The container carries an air-tight glass cover permeable to the radiations in the visible spectrum field.

The container is heated at vacuum state with depression not lower than 0.04 atmospheres.

The ratio value of solvent solution weight / flowers or capsules weight is between 3 and 1 and between 15 and 1 depending on the decreasing water content of flowers or capsules or the their mixtures. After flowers and/or capsule introduction, there is put the solvent chosen between:
a) Neem oil as which;
b) mixtures including Neem oil and a solvent or solvents mixtures, such as benzyl alcohol, ethanol, phenylethyl alcohol, alphaphenylethyl alcohol, ethyl alcohol, isopropyl alcohol, octyl alcohol; glycols as glycerin, propylene glycol, polyethylene glycol; esters as ethyl acetate, octyl acetate, ethyl lactate, isopropyl acetate, isopropyl myristate, isopropyl palmitate, ethyl caprylate, ethylphenylacetate, ethyl oleate, ethyl linoleate, ethyl laurate, triethylcitrate, phenylethyl acetate; triglycerides as: triolein, trilinolein, tributyrin, triacetin, tricaprylin, tricaproin, tricaprin, paraffin oils, silicones, in ratio Neem oil-solvents between 1:2 and 1:0.01.

The listed extraction solvents at items a, b, alone or added with components such as silicones, paraffin oils, esters, triglyceride liquids at 4° C., can unfavorable precipitation phenomena in the topic composition during the preservation, widening the applicability range until temperatures close to 0° C. or lower.

Therefore the vacuum is obtained, the heating of mass of the extraction solvent and biomass at temperatures ranging between 16° C. and 100° C. is activated and the helicoidal blades shaft is put into rotation.

The irradiation is activated and it is maintained the contact between extractant solution and biomass for periods from 1 hour until 400 hours.

When the extraction time is elapsed, the maceration liquid is sent, interposing one or more filters, into dark glass amber colored container and therein the maceration product is preserved avoiding the contact with the air oxygen. The extraction kinetics is overseen monitoring, by means of HPLC chromatography, the two molecules of marker hypericine and derivatives with 585 nanometers and the hyperphorine and derivatives with 278 nanometers.

With this method is obtained a composition as anti-inflammatory medicine, antiseptic and cicatrizing, for example in the treatment of outside wounds, ulcers, sores and burns, further acting as repellent for myasis and not insects.

Further features will greatly result from the description of some practical realization preferred examples of the preparation method of the extract according to the invention, examples given hereinafter as indicative and not limitative.

EXAMPLE 1

There are introduced in the reactor 300 grams of *Hypericum* flowers or *Hypericum perforatum* capsules dried, or frozen or lyophilized, etc. and vacuum is obtained after hermetic sealing of the glass cover of the reactor.

Therefore 4 kg of clear Neem oil are introduced, and when completed the solvent feeding, the multiple-blade agitator starts up, the temperature is grown to 50° C. and there is radiation.

After 220 hour the mixing shaft is stopped, and simultaneous is blocked the heating and the radiation and the extract is transferred into an amber colored glass container.

One or two filtering cartridges for eliminating the suspension material are inserted in the adducing pipe of the extract. The *Hypericum* extract in Neem oil is preserved at dark at 20° C.±1.

The extract yield was 2.85 kg equal to 71.25% of the introduced Neem oil.

EXAMPLE 2

300 grams of lyophilized *Hypericum* flowers (about 2 liters of volume) of which 60% are infructescence are introduced into the reactor and 3.5 kg of extractant solution are added, consisting of Neem oil 41% (weight/weight), 26% of ethyl acetate, 16% of benzyl alcohol, 16% of ethanol at 96%.

The vacuum is obtained, it is programmed the heating to 35° C. and the mixing speed is adjusted by fixing the rotation speed of the shaft supporting the blades, by radiating with white light lamps, for a total extraction time of 180 hours.

After such period, agitation and irradiation are stopped and the extract is transferred into amber colored glass container.

The recovered extract weight was of 2.8 kg equal to a yield of 80.3% of the extractant mixture.

EXAMPLE 3

800 grams of *Hypericum* capsules or fresh *Hypericum* flowers are placed into reactor, both 3.8 kg of extractant solution of the following per cent composition: 50% of Neem oil, 15% of alcohol phenyl ethylic, 20% of propyl acetate, 10% of ethanol at 96°, 2% of isopropyl palmitate, 3% of paraffin oil with freezing point at −20° C. and the vacuum is obtained.

The heating is fixed to 65° C., the agitator is activated and, giving the irradiation, the extraction is continued for 120 hours.

The agitation and the irradiation are stopped and the trial continues according to example 1 by transferring into dark glass container 2.3 kg of extract equal to a yield of 71.8%.

An advantage is to increase the extraction method for example by using a solvent.

An additional advantage is to obtain *Hypericum* extract in Neem oil concentrates.

The invention claimed is:

1. A method for preparing a *Hypericum perforatum* extract in Neem oil comprising:
   combining an amount of *Hypericum* flowers and/or encapsulated *Hypericum* flowers with a quantity of an extraction solvent being Neem oil present in a weight ratio ranging between 1:3 and 1:15 to provide a mixture;
   introducing the mixture into a reactor; and
   maintaining the mixture under vacuum and agitating for a predefined time ranging between one hour and 400 hours and at a temperature ranging between 16° C. and 100° C. to produce a macerated product which contains the *Hypericum perforatum* extract dissolved in the Neem oil.

2. The method according to claim 1 further comprising irradiating the mixture with light having a visible spectrum.

3. The method according to claim 1 wherein the *Hypericum* flowers are fresh, frozen, lyophilized or dried *Hypericum* flowers.

4. The method according to claim 1 wherein the vacuum has a depression not lower than 0.04 atmospheres.

5. The method according to claim 1 wherein the agitation is variable between 2 and 30 rotations per hour.

6. The method according to claim 1 wherein the Neem oil is provided in combination with a solvent or a solvent mixture.

7. The method according to claim 6 wherein the Neem oil comprises at least 33% by weight of the combination with the solvent or mixture of solvents.

8. The method according to claim 6 wherein the solvent is selected from the group consisting of alcohols, glycols, esters, triglycerides, paraffin oils, silicones or combinations thereof.

9. The method according to claim 6 wherein the solvent is selected from the group consisting of benzyl alcohol, ethanol, phenylethyl alcohol, alphaphenylethyl alcohol, ethyl alcohol, isopropyl alcohol, octyl alcohol, glycerin, propylene glycol, polyethylene glycol, ethyl acetate, octyl acetate, ethyl lactate, isopropyl acetate, isopropyl myristate, isopropyl palmitate, ethyl caprylate, ethylphenylacetate, ethyl oleate, ethyl linoleate, ethyl laurate, triethylcitrate, phenylethyl acetate, triolein, trilinolein, tributyrin, triacetin, tricaprylin, tricaproin, tricaprin or combinations thereof.

10. The method according to claim 1 further comprising transferring the extract, after an extraction time has elapsed, into a dark amber colored glass container.

11. The method according to claim 10 further comprising filtering the extract during the transferring to remove suspension material.

12. The method according to claim 1 further comprising preserving the extract by avoiding contact with oxygen in the air.

13. A composition comprising a *Hypericum perforatum* extract in Neem oil obtained by the method of claim 1.

14. The composition according to claim 13 characterized in that the composition is usable as a liquid lotion at a temperature at least as low as 0° C.

15. The composition according to claim 13 wherein the extract is obtained from *Hypericum* flowers or encapsulated *Hypericum* flowers which are fresh or frozen or lyophilized or triturated before the maceration.

* * * * *